US00PP25288P2

(12) United States Plant Patent
Heuger

(10) Patent No.: US PP25,288 P2
(45) Date of Patent: Feb. 10, 2015

(54) ***HELLEBORUS* PLANT NAMED 'COSEH 1030'**

(50) Latin Name: *Helleborus niger*
Varietal Denomination: COSEH 1030

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 125 days.

(21) Appl. No.: 13/815,560

(22) Filed: Mar. 8, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 1030', characterized by its upright and mounding plant habit; uniform and freely flowering habit; dark green-colored leaves; freely flowering habit; single white-colored flowers; and good garden performance.

2 Drawing Sheets

Botanical designation: *Helleborus niger.*
Cultivar denomination: 'COSEH 1030'.

BACKGROUND OF THE INVENTION

The present invention relates to a new and distinct cultivar of *Helleborus* plant, botanically known as *Helleborus niger* and hereinafter referred to by the name 'COSEH 1030'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in November, 2006 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in December, 2008.

Asexual reproduction of the new *Helleborus* plant by divisions in a controlled greenhouse environment in Glandorf, Germany since March, 2009 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 1030'. These characteristics in combination distinguish 'COSEH 1030' as a new and distinct *Helleborus* plant:

1. Upright and mounding plant habit.
2. Uniform and freely flowering habit.
3. Dark green-colored leaves.

4. Freely flowering habit.
5. Single white-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger* 'HGC Josef Lemper', disclosed in U.S. Plant Pat. No. 15,615. In side-by-side comparisons conducted in Glandorf, Germany, plants of the new *Helleborus* differed primarily from plants of 'HGC Josef Lemper' in the following characteristics:

1. Plants of the new *Helleborus* had darker green-colored leaves than plants of 'HGC Josef Lemper'.
2. Plants of the new *Helleborus* had smaller flowers than plants of 'HGC Josef Lemper'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 1030' grown in a container.

The photograph on the second sheet is a close-up view of a typical flower of 'COSEH 1030'.

DETAILED BOTANICAL DESCRIPTION

The aforementioned photographs and following observations, measurements and values describe plants grown during the late autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C.

Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger* 'COSEH 1030'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures about 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; low vigor to moderately vigorous growth habit.

*Plant height*.—About 20.2 cm.

*Plant diameter* (*area of spread*).—About 30.6 cm.

Foliage description:

*Arrangement*.—Leaves arranged in a basal rosette; leaves palmately compound with seven leaflets per leaf.

*Leaf length*.—About 10.8 cm.

*Leaf width*.—About 12.1 cm.

*Leaflet length*.—About 7.1 cm.

*Leaflet width*.—About 2.7 cm.

*Leaf shape*.—Palmate; orbicular in outline.

*Leaflet shape*.—Obovate to oblanceolate.

*Leaflet apex*.—Acute.

*Leaflet base*.—Cuneate.

*Leaflet margin*.—Serrate.

*Leaflet texture, upper and lower surfaces*.—Smooth, glabrous; leathery.

*Leaflet venation pattern*.—Pinnate.

*Leaflet color*.—Developing leaves, upper surface: Close to N137D. Developing leaves, lower surface: Close to 138B. Fully developed leaves, upper surface: Close to N137A; venation, close to 144C, at the base, tinged with close to 200B to 200C. Fully developed leaves, lower surface: Close to 147B; venation, close to 150B to 150C tinged with close to 176B.

*Petioles*.—Length: About 12.5 cm. Diameter: About 5 mm. Texture, upper and lower surfaces: Smooth, glabrous. Color, upper and lower surfaces: Close to 144C, heavily dotted with close to N186C, dots lighter in color, close to 187D, towards the base.

Flower description:

*Flower shape and habit*.—Single rotate flowers arranged singly or in pairs, rarely three; freely and uniform flowering habit with about 50 flowers and flower buds developing per plant; flowers facing outwardly to slightly upright and nodding.

*Fragrance*.—None detected.

*Natural flowering season*.—Plants begin flowering about ten months after planting; plants flower from late autumn into the winter in Germany.

*Flower longevity on the plant*.—About ten days; flowers not persistent.

*Flower buds*.—Length: About 2 cm. Diameter: About 1.1 cm. Shape: Ovate. Color: Close to NN155A; towards the base, close to 157D.

*Flower diameter*.—About 6.9 cm.

*Flower depth* (*height*).—About 2.1 cm.

*Petals*.—Transformed into nectaries.

*Sepals*.—Quantity and arrangement: Five, arranged in a single whorl. Length: About 3.8 cm. Width: About 3.4 cm. Shape: Broadly ovate to orbicular. Apex: Obtuse. Base: Broadly cuneate. Margin: Entire. Texture, upper and lower surfaces: Smooth, glabrous. Color: When opening, upper and lower surfaces: Close to NN155D. Fully opened, upper and lower surfaces: Close to NN155B; color becoming closer to 145C to 145D with development.

*Peduncles*.—Length: About 14.7 cm. Diameter: About 6 mm. Aspect: About 10° from vertical. Strength: Strong. Texture: Smooth, glabrous. Color: Close to N144A, heavily dotted with close to 187A.

*Pedicels*.—Length: About 2.7 cm. Diameter: About 3 mm. Aspect: About 35° from peduncle axis. Strength: Moderately strong. Texture: Smooth, glabrous. Color: Close to 151A, heavily dotted with close to 187D.

*Reproductive organs*.—Stamens: Quantity per flower: About 100. Filament length: About 1.3 cm. Filament color: Close to NN155D. Anther shape: Reniform. Anther length: About 2 mm. Anther color: Close to 3A to 3B. Pollen amount: Abundant. Pollen color: Close to 2D. Pistils: Quantity per flower: About nine. Pistil length: About 7 mm. Stigma shape: Club-shaped. Stigma color: Close to 155A. Style length: About 6 mm. Style color: Close to 63C to 63D. Ovary color: Close to 150C to 150D. Nectaries (transformed petals): Quantity per flower: About 13. Length: About 1.2 cm. Diameter: About 4 mm. Shape: Narrow triangular, flattened tubular. Color, immature, inner and outer surfaces: Close to 144B. Color, mature, inner and outer surfaces: Close to N144A; towards the apex, close to 5B; with development, color becomes closer to 151A.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 1030' as illustrated and described.

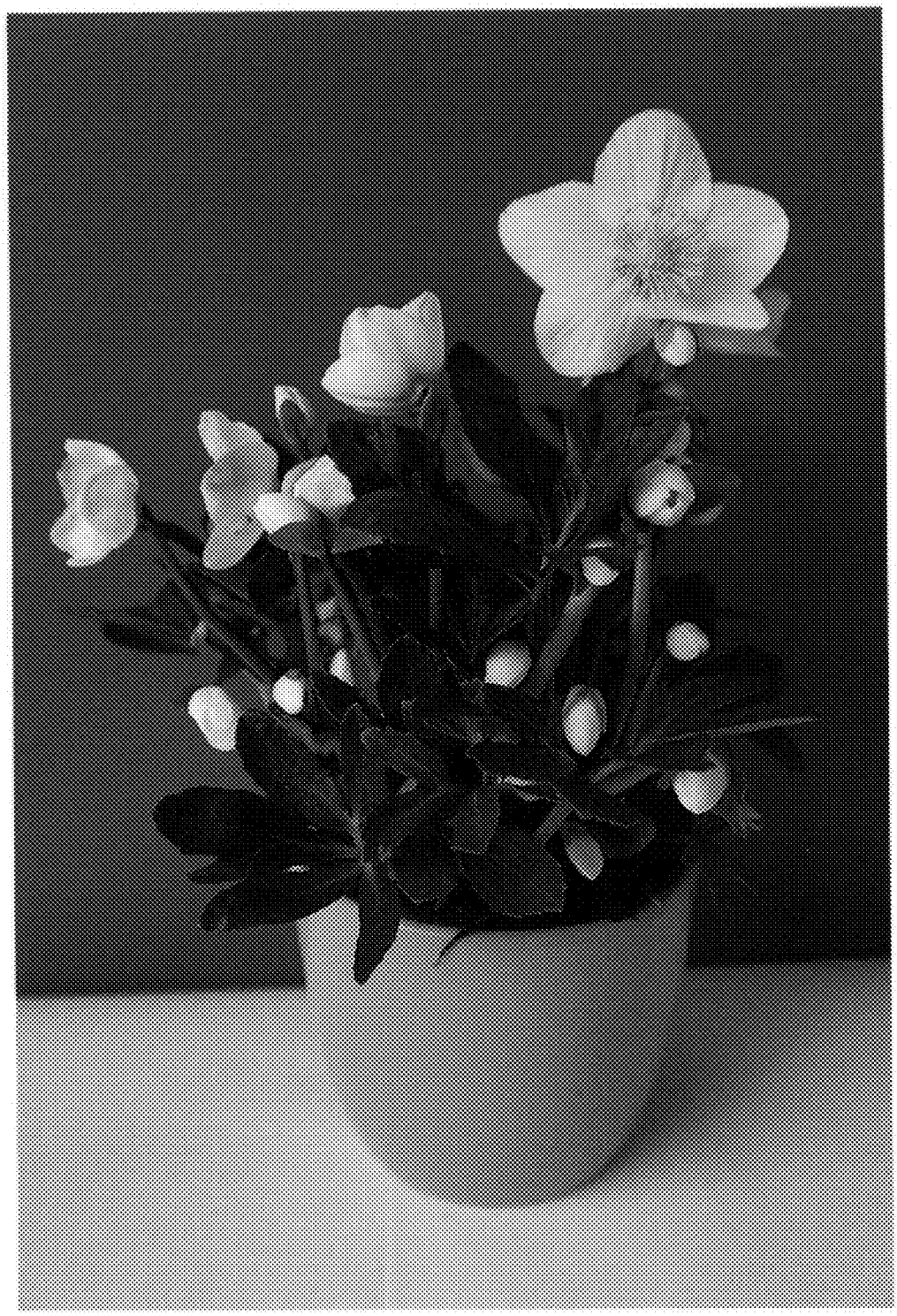

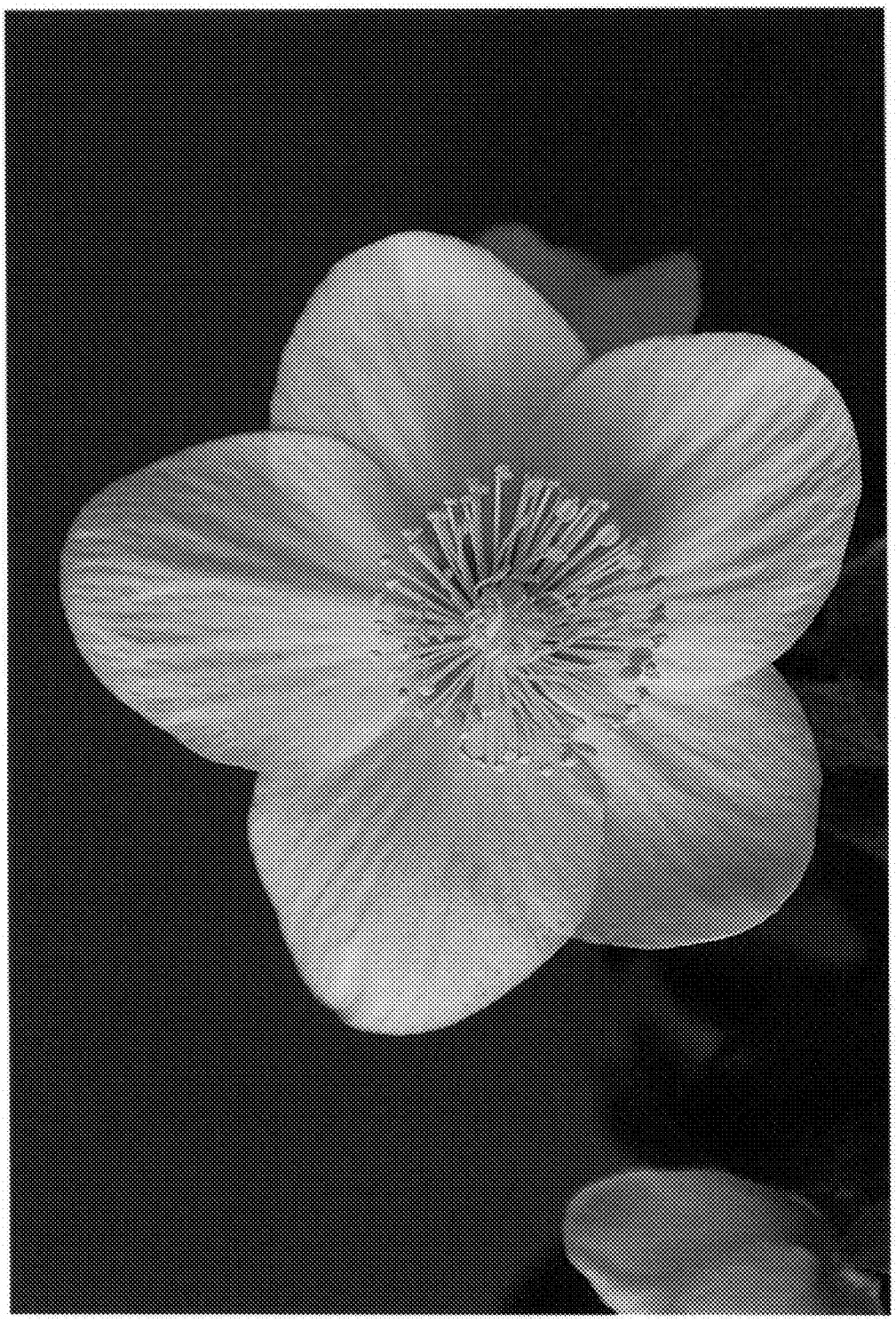

* * * * *